US009447063B2

(12) United States Patent
Won et al.

(10) Patent No.: US 9,447,063 B2
(45) Date of Patent: Sep. 20, 2016

(54) DISUBSTITUTED ADAMANTYL DERIVATIVE OR PHARMACEUTICALLY ACCEPTABLE SALT THEREOF, PRODUCTION METHOD FOR SAME, AND PHARMACEUTICAL COMPOSITION FOR SUPPRESSING CANCER METASTASIS COMPRISING SAME AS ACTIVE INGREDIENT

(71) Applicants: KOREA RESEARCH INSTITUTE OF BIOSCIENCE AND BIOTECHNOLOGY, Daejeon (KR); DONGGUK UNIVERSITY INDUSTRY-ACADEMIC COOPERATION FOUNDATION, Seoul (KR)

(72) Inventors: Mi Sun Won, Daejeon (KR); Kyeong Lee, Seoul (KR); Bo Kyung Kim, Daejeon (KR); Hyun Seung Ban, Daejeon (KR); Seohyun Son, Goyang-si (KR); Kyung-Sook Chung, Daejeon (KR)

(73) Assignees: KOREA RESEARCH INSTITUTE OF BIOSCIENCE AND BIOTECHNOLOGY, Daejeon (KR); DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/724,248

(22) Filed: May 28, 2015

(65) Prior Publication Data

US 2015/0259312 A1 Sep. 17, 2015

Related U.S. Application Data

(63) Continuation of application No. PCT/KR2013/009119, filed on Oct. 11, 2013.

(30) Foreign Application Priority Data

Nov. 30, 2012 (KR) ........................ 10-2012-0137902

(51) Int. Cl.

| | |
|---|---|
| ***A61K 31/167*** | (2006.01) |
| ***C07D 307/42*** | (2006.01) |
| ***C07C 235/24*** | (2006.01) |
| ***A61K 45/06*** | (2006.01) |
| ***A61K 31/341*** | (2006.01) |
| ***C07C 231/12*** | (2006.01) |

(52) U.S. Cl.

CPC ........... *C07D 307/42* (2013.01); *A61K 31/167* (2013.01); *A61K 31/341* (2013.01); *A61K 45/06* (2013.01); *C07C 231/12* (2013.01); *C07C 235/24* (2013.01); *C07C 2103/74* (2013.01)

(58) Field of Classification Search

CPC ........................... C07D 307/42; A61K 31/167
USPC ......................................................... 549/496
See application file for complete search history.

(56) References Cited

U.S. PATENT DOCUMENTS

| | | | |
|---|---|---|---|
| 6,462,064 | B1 | 10/2002 | Pfahl et al. |
| 2005/0010052 | A1 | 1/2005 | Alcaraz et al. |
| 2011/0178086 | A1 | 7/2011 | Jimenez et al. |

FOREIGN PATENT DOCUMENTS

| | | | |
|---|---|---|---|
| WO | 2006/024627 | A2 | 3/2006 |
| WO | 2010/059618 | A1 | 5/2010 |
| WO | 2011/014009 | A2 | 2/2011 |

OTHER PUBLICATIONS

Sikic et al., Cancer Chemo. Pharm. (1997) vol. 40 (supplement): S13-S19.*

King, Med. Chem., Principle and Practice (1994), pp. 206-208.*

Yang et al., "Twist activation by hypoxia inducible factor-1 (HIF-1): Implications in metastasis and development", Cell Cycle, vol. 7, No. 14, pp. 2090-2096, (2008).

Davies et al., "A Synthetic Matrix Metalloproteinase Inhibitor Decreases Tumor Burden and Prolongs Survival of Mice Bearing Human Ovarian Carcinoma Xenografts", Cancer Research, vol. 53, pp. 2087-2091, (1993).

* cited by examiner

*Primary Examiner* — Taofiq A Solola

(74) *Attorney, Agent, or Firm* — Vorys, Sater, Seymour & Pease LLP; Mih Suhn Koh

(57) ABSTRACT

The present invention relates to a novel disubstituted adamantyl derivative or the pharmaceutically acceptable salts thereof, a method for preparing the same, and a pharmaceutical anticancer or antimetastasis composition comprising the same as an active ingredient. The disubstituted adamantyl derivative of the present invention suppressed accumulation of HIF-1α, inhibiting the expression of the metastasis related protein Twist dose-dependently. Thus, the disubstituted adamantyl derivative of the invention is effective in inhibiting the expressions of the metastasis related proteins, β-catenin and RohA, and the EMT related genes such as MMP2 and MMP9, without cytotoxicity. Therefore, the disubstituted adamantyl derivative or the pharmaceutically acceptable salts thereof of the invention can be efficiently used as a pharmaceutical anticancer or antimetastasis composition.

7 Claims, 10 Drawing Sheets

DISUBSTITUTED ADAMANTYL DERIVATIVE OR PHARMACEUTICALLY ACCEPTABLE SALT THEREOF, PRODUCTION METHOD FOR SAME, AND PHARMACEUTICAL COMPOSITION FOR SUPPRESSING CANCER METASTASIS COMPRISING SAME AS ACTIVE INGREDIENT

CROSS-REFERENCES TO RELATED APPLICATION

This patent application claims the benefit of priority from Korean Patent Application No. 10-2012-0137902, filed on Nov. 30, 2012.

BACKGROUND OF THE INVENTION

1. Field of the Invention

The present invention relates to a novel disubstituted adamantyl derivative or a pharmaceutically acceptable salt thereof, a method for producing the same, and a pharmaceutical composition for inhibiting cancer metastasis containing the same as an active ingredient 2. Description of the Related Art Even after all the efforts over the past tens of years, cancer is still one of the incurable diseases. The reason why cancer is so difficult to treat is because cancer cells progress malignantly which favors the cancer cell survival and thus they invade in surrounding tissues and eventually move to other organs, that is so called metastasis. Cancer metastasis is a critical reason of death among cancer patients. Approximately ⅓ of patients diagnosed as cancer already have metastatic cancer at the time of diagnosis. Another ⅓ of cancer patients also display a minor or early stage of metastasis even though that is too early to be detected by diagnostic examinations, so that they have a great potential of having metastatic cancer when they are only treated locally for their primary cancers. That is, metastatic cancer is developed from primary cancer actually in ⅔ of cancer patients. Therefore, an efficient treating agent that can prevent and at the same time control cancer metastasis after surgical operation is urgently required.

Cancer metastasis is accomplished by the steps of adhesion, invasion, and angiogenesis. In the step of adhesion, angiopoietin-2, angiopoietin-like-4, Cox-2, MMP-1, MMP-2, MMP-3, MMP-10, PGF, and VEGF can weaken the binding between the vascular cells in the tissue where the cancer cell would want to invade in order for the cancer cells to move in easily from the blood vessel to that tissue, that is they make extravasation easy. Metastasis can be explained by the process of EMT/MET (Epithelial-Mesenchymal Transition/Mesenchymal-Epithelial Transition) which is composed of the following steps; epithelial cells are converted into mesenchymal cells and the converted mesenchymal cells migrate through blood vessels and are landed in another organ; and then the landed mesenchymal cells are converted reversely into epithelial cells. At this time, such genes as Twist, SNAIL, and ID1 induce EMT and accelerate metastasis by endowing cancer stem cell like characteristics thereto.

In the meantime, HIF-1 is the most important molecule in regulating the adaptation of cancer cell under hypoxia. Particularly, the level of HIF-1α protein is closely related to the prognosis of cancer patients. When cancer cells are under hypoxia, the cells induce HIF-1α accumultion, or the mentioned growth factors above can also induce HIF-1α activation. Also, the activation of HIF-1α can be induced by the activation of an oncogene or the inactivation of a tumor suppress gene like pVHL. The activated HIF-1α induces the expressions of hexokinase 2, glucose transporter 1, erythropoietin, IGF-2, endoglin, VEGFA, MMP-2, MMP-9, uPAR, and MDR1, by which cancer cells acquire such characteristics as resistance against apoptosis, promoted angiogenesis, promoted cell proliferation, cell migration, metastasis, invasion, etc, resulting in the malignance of cancer.

HIF-1 also plays an important role in regulating EMT (epithelial-mesenchymal transition) related genes in the course of metastasis. HIF-1 reduces E-cadherin, but increases the expressions of fibronectin, vimentin, and Twist, suggesting that HIF-1 can promote metastasis particularly the stage of EMT. Twist not only plays an important role in gastrulation and mesoderm formation but also increases the expression of metastasis related proteins such as β-catenin and RhoA, etc, so that it has been recognized as a crucial factor for inducing EMT and cell migration (Cell Cycle, 2008, 7. 14, 2090-2096).

Up to date, studies have been actively going on to develop an anticancer agent inhibiting metastasis and also suppressing cancer stem cells by using EMT promoting transcription factors. As a result, numbers of anticancer agents such as Taxol, rapamycin, and 17-AAG (17-allylaminogeldanamycin) have been developed. These anticancer agents are to inhibit the functions of adhesion molecules including integrin family mainly expressed on the surface of cancer cells, which are exemplified by extracellular matrix components like vitronectin, laminin, and fibronectin, or to suppress MMP and type IV collagenase to inhibit metastasis (Cancer Research, 53, 2087-2091, 1993). However, the method to inhibit metastasis by using the conventional anticancer agents is only effective in inhibiting the invasion into other organs of cancer cells that have already traveled through blood stream from the organ where the cancer cells have been originally proliferated. Therefore, this conventional method is not the fundamental treatment method.

In the course of study to find out a compound that can suppress the accumulation of HIF-1α, the present inventors confirmed that the inhibition of HIF-1α resulted in the suppression of Twist expression, leading to the completion of this invention.

SUMMARY OF THE INVENTION

It is an object of the present invention to provide a novel disubstituted adamantyl derivative.

It is another object of the present invention to provide a method for preparing the disubstituted adamantyl derivative.

It is also an object of the present invention to provide a pharmaceutical composition for the inhibition of metastasis comprising the disubstituted adamantyl derivative or the pharmaceutically acceptable salts thereof as an active ingredient.

It is further an object of the present invention to provide a pharmaceutical anticancer composition comprising the disubstituted adamantyl derivative or the pharmaceutically acceptable salts thereof as an active ingredient.

To achieve the above objects, the present invention provides the novel disubstituted adamantyl derivative repre sented by the below formula 1 or the pharmaceutically acceptable salts thereof:

[Formula 1]

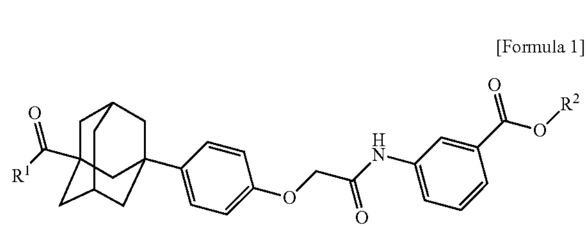

(In the formula 1, $R^1$ and $R^2$ are as defined in this description).

The present invention also provides a method for preparing the disubstituted adamantyl derivative represented by formula 1 wherein the compound represented by formula 2 is reacted with the compound represented by formula 3 to give the compound represented by formula 1, as shown in the below reaction formula 1.

[Reaction Formula 1]

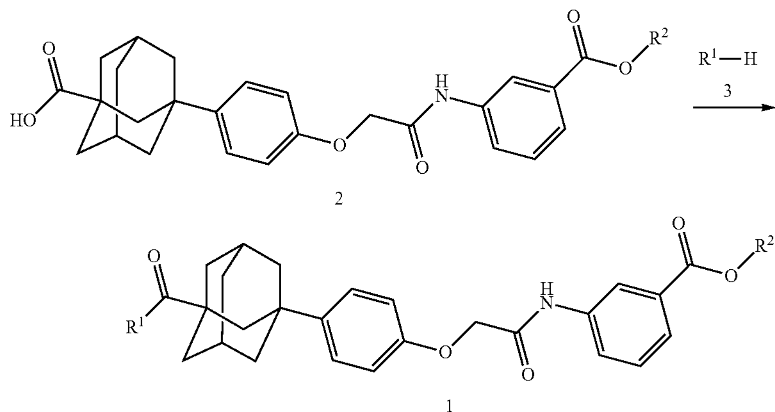

(In the reaction formula 1, $R^1$ and $R^2$ are as defined in this description).

Further, the present invention provides a pharmaceutical composition for the inhibition of metastasis comprising the disubstituted adamantyl derivative represented by formula 1 or the pharmaceutically acceptable salts thereof as an active ingredient.

[Formula 1]

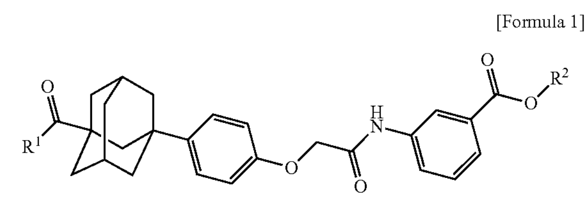

(In the formula 1, $R^1$ and $R^2$ are as defined in this description).

The present invention also provides a pharmaceutical anticancer composition comprising the disubstituted adamantyl derivative represented by formula 1 or the pharmaceutically acceptable salts thereof as an active ingredient.

[Formula 1]

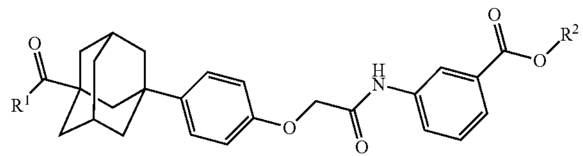

(In the formula 1, $R^1$ and $R^2$ are as defined in this description).

Advantageous Effect

The disubstituted adamantyl derivative of the present invention not only inhibits metastasis-related HIF-1 and accordingly inhibits the expression of metastasis-related protein Twist, β-catenin and RohA and the EMT related genes such as MMP2 and MMP9, suggesting that it is excellent in inhibiting cancer metastasis. In addition, the disubstituted adamantyl derivative of the present invention does not display side effects attributed to cytotoxicity when it is absorbed in a living body, suggesting as an efficient pharmaceutical anticancer composition or antimetastasis composition.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
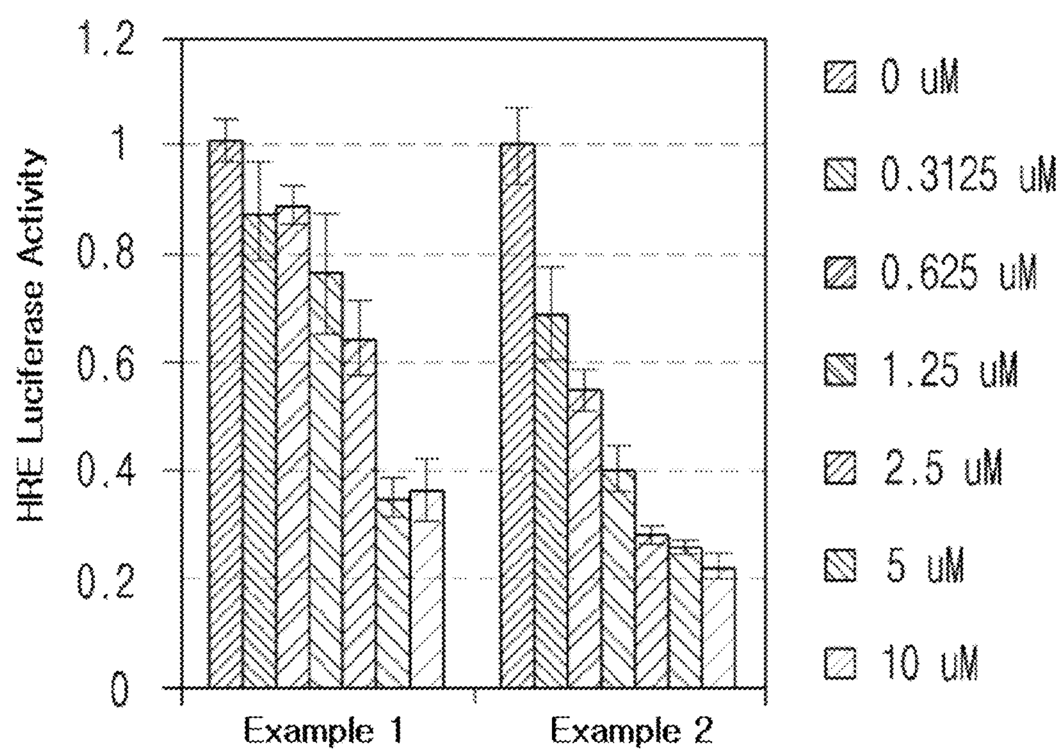
FIG. 1 is a graph illustrating the inhibition of HRE activity according to the concentrations of the compounds prepared in Examples 1 and 2.

Hereinafter, the present invention is described in detail.

The present invention provides the novel disubstituted adamantyl derivative represented by the below formula 1 or the pharmaceutically acceptable salts thereof:

[Formula 1]

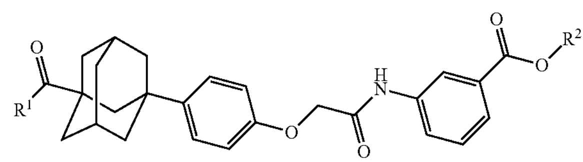

In the formula 1, $R^1$ is —X—$(CH_2)_n$—$R^3$;

$R^2$ is H or C1-C6 straight or branched alkyl;

$R^3$ is unsubstituted or substituted C5-C10 aryl or unsubstituted or substituted heteroaryl, wherein the said heteroaryl is 5-membered or 6-membered heteroaryl containing one or more heteroatoms selected from the group consisting of N, O, and S, the said substituted aryl or heteroaryl can be substituted with one or more halogens; C1-C6 straight or branched alkyl; hydroxy; C1-C6 straight or branched alkoxy; nitro; nitrile; unsubstituted amine or amine substituted with one or more C1-C6 straight or branched alkyls; C1-C6 straight or branched alkylcarbonyl; C1-C6 straight or branched alkoxycarbonyl or 5-membered or 6-membered heterocycloalkyl containing heteroatoms selected from the group consisting of N, O, and S;

X can be NH or O; at this time, when $R^3$ is unsubstituted or substituted aryl, X is O; and n is an integer of 1-5.

Preferably, $R^1$ is —X—$(CH_2)_n$—$R^3$;

$R^2$ is H or C1-C4 straight or branched alkyl;

$R^3$ is unsubstituted or substituted phenyl, unsubstituted or substituted pyridine, pyrazine, imidazole, thiophene, benzothiophene, furan, or benzofuran, wherein the said substituted phenyl or the substituted pyridine, pyrazine, imidazole, thiophene, benzothiophene, furan or benzofuran can be substituted with one or more fluoro, bromo, chloro, methyl, ethyl, propyl, isopropyl, butyl, hydroxy, t-butyl, methoxy, ethoxy, propoxy, butoxy, nitro, nitrile, amine, methylamine, dimethylamine, ethylamine, diethylamine, acetyl, ethylcarbonyl, methoxycarbonyl, ethoxycarbonyl, or 5-membered or 6-membered heterocycloalkyl comprising heteroatoms selected from the group consisting of N, O, and S;

X can be NH or O; at this time, when $R^3$ is unsubstituted or substituted phenyl, X is O; and n is an integer of 1-3.

More preferably, $R^1$ is —X—$(CH_2)_n$—$R^3$;

$R^2$ is methyl;

$R^3$ is unsubstituted or substituted phenyl, or unsubstituted or substituted furan, wherein the said substituted phenyl or the substituted heteroaryl can be substituted with one or more chloro, bromo, methyl, ethyl, hydroxy, methoxy, ethoxy, ethylamine, acetyl, piperidine, piperazine, pyrolidine, tetrahydrofuran, or tetrahydrothiophene;

X can be NH or O; at this time, when $R^3$ is unsubstituted or substituted phenyl, X is O; and n is an integer of 1-3.

Most preferably, the disubstituted adamantyl derivative represented by formula 1 is as follows:

(1) methyl-3-(2-(4-(3-((furan-2-ylmethoxy)carbonyl)adamantane-1-yl)phenoxy)acetamido)benzoate; or (2) methyl-3-(2-(4-(4-((3,4-dimethoxybenzyloxy)carbonyl)adamantane-1-yl)phenoxy)acetamido)benzoate.

The disubstituted adamantyl derivative represented by formula 1 of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the disubstituted adamantyl derivative represented by formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in the organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution, and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the disubstituted adamantyl derivative represented by formula and the pharmaceutically acceptable salts thereof but also solvates, hydrates, or isomers possibly produced from the same.

The present invention also provides a method for preparing the disubstituted adamantyl derivative represented by formula 1 wherein the compound represented by formula 2 is reacted with the compound represented by formula 3 to give the compound represented by formula 1, as shown in the below reaction formula 1.

[Reaction Formula 1]

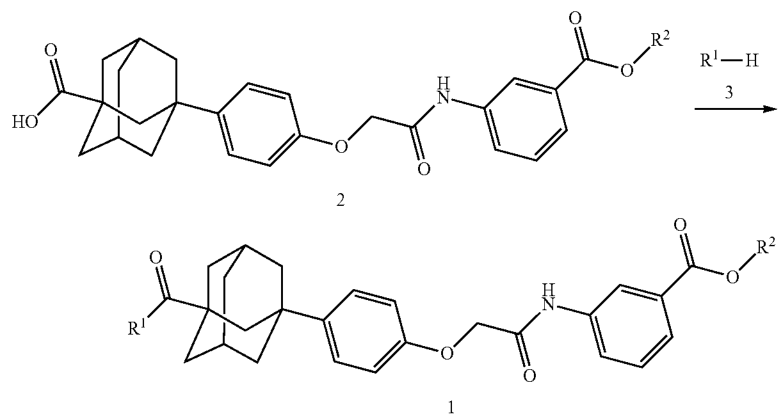

(In the reaction formula 1, $R^1$ and $R^2$ are as defined in formula 1).

The method for preparing the disubstituted adamantyl derivative represented by formula 1 of the present invention is to prepare the compound represented by formula 1 via the coupling reaction between carboxyl group of the compound represented by formula 2 and the compound represented by formula 3 in the presence of a base and a coupling agent.

At this time, as the coupling agent used in the above coupling reaction, diisopropylethylamine (DIPEA), triethylamine (TEA), or dimethylaminopyridine (DMAP) can be used along with benzotriazole-1-yl-oxy-tris(dimethylamino)-phosphoniumhexafluorophosphate (Py-BOP), O-benzotriazole-N,N,N,N-tetramethyl-uronium-hexafluoro-phosphate (HBTU), 2-(7-aza-1H-benzotriazole-1-yl)-1,1,3,3-tetramethyluroniumhexafluorophosphate (HATU), hydroxybenzotriazole (HOBt), dicyclohexylcarbodiimide (DCC), 1-ethyl-3-(3-dimethylaminopropyl)carbodiimide (EDC), or carbonyldiimidazole (CDI), and more preferably DIPEA, TEA, or DMAP can be used together with hydroxybenzotriazole (HOBt) and 1-ethyl-3-(3-dimethylaminopropyl)carbodiimide (EDC).

The organic solvent used herein is exemplified by methanol, tetrahydrofuran (THF), dimethylformamide (DMF), dichloromethane (DCM), and toluene, which do not affect the reaction, and more preferably dimethylformamide (DMF) can be used.

Further, the present invention provides a pharmaceutical composition for the inhibition of metastasis comprising the disubstituted adamantyl derivative represented by formula 1 or the pharmaceutically acceptable salts thereof as an active ingredient.

[Formula 1]

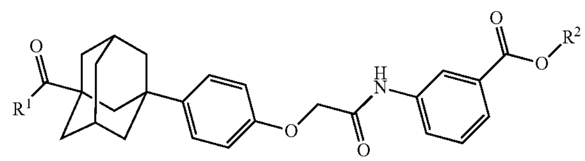

(In the formula 1, $R^1$ and $R^2$ are as defined in formula 1).

The following experiment was performed to investigate the inhibitory effect of the disubstituted adamantyl derivative represented by formula 1 of the present invention on cancer cell metastasis by suppressing the accumulation of HIF-1α. As a result, it was confirmed that the disubstituted adamantyl derivative of the present invention suppressed accumulation of HIF-1α leading inhibition of the expression of the metastasis related protein Twist, β-catenin, RohA and EMT related genes such as MMP2 and MMP9.

Therefore, the anticancer activity to inhibit the cancer cell growth and metastasis of the compound of the present invention was not attributed to the non-selective cytotoxicity but attributed to the selective inhibition of the expression of Twist (see Experimental Examples 1-8).

The disubstituted adamantyl derivative of the present invention could inhibit the expression of the metastasis-related protein, Twist, dose-dependently by inhibiting metastasis related HIF-1, so that it displayed not only metastasis inhibiting effect by suppressing the expression of metastasis-related proteins like β-catenin, Twist, and RohA and EMP related genes like MMP2 and MMP9 but also no side effects caused by cytotoxicity, indicating that the compound could be efficiently used as a pharmaceutical anticancer composition or a pharmaceutical composition for inhibiting metastasis.

In the pharmaceutical composition for inhibiting metastasis or the pharmaceutical anticancer composition of the present invention, the said cancer is a solid cancer, which is exemplified by colorectal cancer, liver cancer, stomach cancer, breast cancer, colon cancer, bone cancer, pancreatic cancer, head & neck cancer, uterine cancer, ovarian cancer, rectal cancer, esophageal cancer, small bowel cancer, anal cancer, colon cancer, fallopian tube carcinoma, endometrial carcinoma, uterine cervical carcinoma, vaginal carcinoma, vulval carcinoma, Hodgkin's disease, prostate cancer, bladder cancer, kidney cancer, ureter cancer, renal cell carcinoma, renal pelvic carcinoma, and central nervous system tumor.

The present invention also provides a pharmaceutical anticancer composition comprising the disubstituted adamantyl derivative represented by formula 1 or the pharmaceutically acceptable salts thereof as an active ingredient.

[Formula 1]

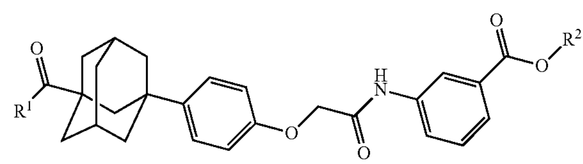

(In the formula 1, $R^1$ and $R^2$ are as defined in formula 1).

The following experiment was performed to investigate whether or not the disubstituted adamantyl derivative represented by formula 1 of the present invention could inhibit the expression of Twist gene by inhibiting HIF-1α accumulation under hypoxia. As a result, the compound of the present invention was confirmed to have the dose-dependent inhibitory effect on HRE activity, and thereby it could inhibit the expression of Twist protein involved in metastasis and cancer cell proliferation. Therefore, it was confirmed that the anticancer activity to inhibit the cancer cell growth and metastasis of the compound of the present invention was not attributed to the non-selective cytotoxicity but attributed to the selective inhibition of the expression of Twist (see Experimental Examples 1-8).

The disubstituted adamantyl derivative of the present invention inhibited accumulation of HIF-1α to suppress the expression of Twist protein dose-dependently, suggesting that the compound was not only excellent in inhibiting metastasis and cancer cell proliferation but also free from side effects caused by cytotoxicity when it was absorbed in a living body. Therefore, it could be efficiently used as a pharmaceutical anticancer composition.

The pharmaceutical composition comprising the disubstituted adamantyl derivative of formula 1 or the pharmaceutically acceptable salts thereof as an active ingredient of the present invention can be administered orally or parenterally and be used in general forms of pharmaceutical formulation, but not always limited thereto.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the disubstituted adamantyl derivative of formula 1 as an active ingredient of the present invention can be administered by parenterally and the parenteral administration includes subcutaneous injection, intravenous injection, intramuscular injection and intrathoracic injection.

To prepare the composition as a formulation for parenteral administration, the disubstituted adamantyl derivative represented by formula 1 or the pharmaceutically acceptable salts thereof of the present invention are mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method. The effective dosage of the pharmaceutical composition comprising the disubstituted adamantyl derivative represented by formula 1 as an active ingredient of the present invention is 0.01-200 mg/kg per day, which can be administered orally or parenterally several times a day or preferably once a day or three times a day.

The pharmaceutical composition of the present invention can be administered alone or together with surgical operation, hormone therapy, chemo-therapy and biological regulators.

Practical and presently preferred embodiments of the present invention are illustrative as shown in the following Examples.

However, it will be appreciated that those skilled in the art, on consideration of this disclosure, may make modifications and improvements within the spirit and scope of the present invention.

1. Analysis Devices

The analysis devices used in this invention to investigate the structure of the product of the invention were as follows.

For nuclear magnetic resonance ($^1H$ NMR), Varian 300 MHz spectrometer and Varian 400 MHz spectrometer were used. $CDCl_3$, MeOH-$d_4$, and DMSO-$d_6$ were used as NMR solvents.

2. TLC and Column Chromatography

Thin layer chromatography (TLC) was performed with 0.25 mm silica plate (Merck F254), the product of E. Merck Co. Silica gel used for column chromatography was Merck Em9385, 230-400 mesh. To investigate the material separated on TLC, UV lamp (=254 nm) was used or the material was exposed on iodine vapor. Or the material was soaked in PMA, ninhydrin solution, p-anisaldehyde, or $KMnO_4$ to induce color development, followed by heating.

3. Reagents

The reagents used in this invention were purchased from Sigma-Aldrich, Lancaster, Fluka, and TCl. Tetrahydrofuran (THF) used for the reaction was prepared by the reaction between Na metal and benzophenone in argon environment via heat-refluxing. When THF turned blue, it was used. Dichloromethane ($CH_2Cl_2$) was reacted with $CaH_2$ in argon environment via heat-refluxing. Other solvents used herein were the 1$^{st}$ degree reagents purchased from Sigma-Aldrich, which were used without being purified. Ethylacetate and n-hexane were purified by heat-refluxing in argon environment before being used.

Manufacturing Example 1

Preparation of 3-bromo-adamantane-1-carboxylic acid

A two-neck round bottom flask was connected to a reflux condenser, to which aluminum chloride ($AlCl_3$, 7.15 mmol) was injected, followed by cooling at −5° C. in argon environment. Then, bromine ($Br_2$, 66 mmol) was added thereto, followed by stirring for 15 minutes. 1-adamantanecarboxylic acid (5.5 mmol) was added to the reaction mixture at a time, followed by stirring for 1 hour with maintaining the temperature at −5° C. The reaction mixture was then additionally stirred for 48 hours with raising the temperature slowly to room temperature. Upon completion of stirring, ice water was poured to the mixture to terminate the reaction. Excessive bromine was de-colored by adding sodium pyrosulfite. The de-colored reactant was extracted by using chloroform. The extracted organic layer was dried over sodium sulfate, followed by concentration under reduced pressure to give the target compound (5.016 mmol, 92.83%).

$^1$H NMR (300 MHz, $CDCl_3$): δ 2.49 (2H, s), 2.36-2.22 (6H, m), 1.9 (2H, m), 1.71 (2H, s).

Manufacturing Example 2

Preparation of 3-(4-methoxyphenyl)adamantane-1-carboxylic acid

Aluminum chloride ($AlCl_3$, 7.7 mmol) was dissolved in anisol (96.25 mmol), which was cooled down at −10° C. The compound prepared in Manufacturing Example 1 (3.85 mmol) was added thereto, followed by stirring for 24 hours with raising the temperature slowly to room temperature. Upon completion of stirring, ice water in which hydrochloric acid (3.3 ml) was dissolved was poured to the reaction mixture to terminate the reaction, followed by extraction with ethylacetate (EA). The extract was then dried over sodium sulfate. The dried reactant was concentrated under reduced pressure, followed by solidification with hexane. The obtained solid was filtered to give the target compound (2.968 mmol, 77%).

$^1$H NMR (300 MHz, $CDCl_3$): δ 7.29 (2H, d, J=8.7 Hz), 6.87 (2H, d, J=8.7 Hz), 3.79 (3H, s), 2.23-1.73 (14H, m).

Manufacturing Example 3

Preparation of 3-(4-hydroxyphenyl)adamantane-1-carboxylic acid

The compound (3.5 mmol) prepared in Manufacturing Example 2 was dissolved in dichloromethane (DCM), followed by cooling at −10° C., to which borontribromide ($BBr_3$, 1.0 M dichloromethane solution, 2.5 equivalent) was loaded in argon environment. Upon completion of the loading, the temperature was raised to room temperature while stirring for 3 hours. Then, cold water was poured to the reaction mixture to terminate the reaction. The reactant was extracted with ethylacetate, and then the extract was dried over sodium sulfate. The dried extract was concentrated under reduced pressure, and purified by column chromatography to give the target compound (2.57 mmol, 73.6%).

$^1$H NMR (300 MHz, DMSO-$d_6$): δ 12.00 (1H, bs), 9.12 (1H, bs), 7.14 (2H, d, J=8.7 Hz), 6.69 (2H, d, J=8.7 Hz), 2.12-1.65 (14H, m).

Manufacturing Example 4

Preparation of 3-(4-hydroxyphenyl)adamantane-1-carboxylic acid

The compound (2.46 mmol) prepared in Manufacturing Example 3 was dissolved in dimethylformamide (3.5 ml), to which anhydrous potassiumbicarbonate ($KHCO_3$, 2.95 mmol) was added, followed by stirring at room temperature for 15 minutes. Benzylbromide (3.7 mmol) was added thereto, followed by stirring for 4 more hours with raising the temperature to 40° C. Upon completion of the stirring, the reaction mixture was diluted in saturated sodiumbicarbonate solution, followed by extraction with ethylacetate (EA). The extract was dried over sodium sulfate. The dried reactant was purified by column chromatography to give the target compound (154 mmol, 62.6%).

$^1$H NMR (300 MHz, DMSO-$d_6$): δ 9.12 (1H, bs), 7.36 (5H, m), 7.14 (2H, d, J=8.7 Hz), 6.69 (2H, d, J=8.7 Hz), 5.08 (2H, s), 2.14-1.66 (14H, m).

Manufacturing Example 5

Preparation of 3-(4-ethoxycarbonylmethoxyphenyl) adamantane-1-carboxylic acid benzylester The compound (0.55 mmol) prepared in Manufacturing Example 4, potassiumcarbonate (0.66 mmol), and ethylchloroacetate (1.65 mmol) were dissolved in dimethylformamide (DMF, 1 ml), followed by stirring at room temperature for overnight. Upon completion of the reaction, the reaction mixture was diluted in ethylacetate (EA) and then washed with saturated sodiumbicarbonate and brine, followed by drying over sodium sulfate. The dried reactant was purified by column chromatography to give the target compound (0.533 mmol, 96.7%).

$^1$H NMR (300 MHz, $CDCl_3$): δ 7.35 (5H, m), 7.28 (2H, d, J=8.7 Hz), 6.87 (2H, d, J=8.7 Hz), 5.11 (2H, s), 4.59 (2H, s), 4.30 (2H, q, J=7.5 Hz), 2.22-1.71 (14H, m), 1.32 (3H, t, J=7.2 Hz).

Manufacturing Example 6

Preparation of 3-(4-carboxymethoxyphenyl)adamantane-1-carboxylic acid benzylester The compound prepared in Manufacturing Example 5 (0.512 mmol) was dissolved in the mixed solution of tetrahydrofuran/distilled water (1:1) (2.5 ml), to which lithiumhydroxide monohydrate (LiOH $H_2O$, 1.024 mmol), followed by stirring at room temperature for 2 hours. Upon completion of stirring, the reaction mixture was neutralized with 10% hydrochloric acid, followed by extraction with ethylacetate (EA). The extracted organic layer was dried over sodium sulfate, followed by concentration under reduced pressure. The concentrated reactant was purified by column chromatography to give the target compound (0.33 mmol, 65%).

$^1$H NMR (300 MHz, $CD_3OD$): δ 7.34 (5H, m), 7.28 (2H, d, J=8.7 Hz), 6.88 (2H, d, J=8.7 Hz), 5.10 (2H, s), 4.58 (2H, s), 4.30 (2H, q, J=7.5 Hz), 2.19-1.75 (14H, m).

Manufacturing Example 7

Preparation of 3-(4-[(3-methoxycarbonylphenylcarbamoyl)methoxy]phenyl}adamantane-1-carboxylic acid benzylester The compound (0.33 mmol) prepared in Manufacturing Example 6, 3-aminobenzoic acid methylester (0.66 mmol), benzotriazole-1-yl-oxy-tris(dimethylamino)-phosphoniumhexafluorophosphate (Py-BOP, 0.66 mmol), and dimethylaminopyridine (DMAP, 0.66 mmol) were dissolved in dimethylformamide (DMF, 1 ml), followed by stirring at room temperature for overnight. Upon completion of stirring, the reaction mixture was diluted in ethylacetate (EA) and then washed with 10% hydrochloric acid, brine, and water, followed by drying over sodium sulfate. The dried reactant was purified by column chromatography to give the target compound (0.25 mmol, 75.3%).

$^1$H NMR (300 MHz, $CDCl_3$): δ 8.38 (1H, s), 8.07 (1H, s), 8.01 (1H, d), 7.83 (1H, d), 7.45 (1H, t, J=8.0 Hz), 7.31-7.38 (7H, m), 6.96 (2H, d), 5.12 (2H, s), 4.61 (2H, s), 3.93 (3H, s), 2.24 (2H, s), 2.04 (2H, s), 1.92 (5H, t, J=15.2 Hz), 1.88 (4H, s), 1.74 (2H, s).

Manufacturing Example 8

Preparation of 3-(4-[(3-carboxyphenylcarbamoyl)methoxy]phenyl}adamantane-1-carboxylic acid benzylester The compound prepared in Manufacturing Example 7 was dissolved in the mixed solution of tetrahydrofuran/distilled water/dioxane=1:1:1 (2.5 ml), to which lithiumhydroxide monohydrate (LiOH $H_2O$, 0.18 mmol) was added, followed by stirring at room temperature for 4 hours. Upon completion of stirring, the reaction mixture was diluted in ethylacetate (EA) and then neutralized with 10% hydrochloric acid, followed by washing with brine. The organic layer was extracted from the washed reactant, which was dried over sodium sulfate and concentrated under reduced pressure. The concentrated reactant was purified by column chromatography to give the target compound (0.072 mmol, 80.03%).

$^1$H NMR (300 MHz, DMSO-$d_6$): δ 13.00 (1H, bs), 10.24 (1H, s), 8.27 (1H, s), 7.88 (1H, d, J=8.7 Hz), 7.66 (1H, d, J=8.1 Hz), 7.46 (1H, t, J=8.1 Hz), 7.37 (7H, m), 6.95 (2H, d, J=8.1 Hz), 5.09 (2H, s), 4.67 (2H, s), 2.16-1.67 (14H, m).

Example 1

Preparation of methyl-3-(2-(4-(3-((furan-2-yl-methoxy)carbonyl)adamantane-1-yl)phenoxy)acetamido)benzoate

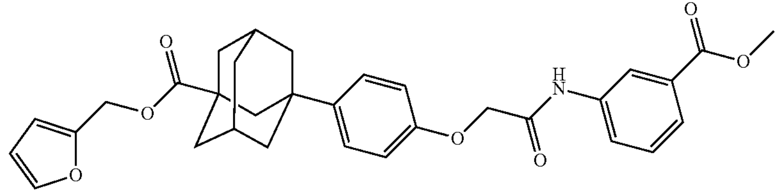 [SMILES: COC(=O)c1cccc(NC(=O)COc2ccc(C34CC5CC(CC(C(=O)OCc6ccco6)(C5)C3)C4)cc2)c1]

The compound (60 mg, 0.13 mmol) prepared in Manufacturing Example 8 was dissolved in tetrahydrofuran, which was cooled down at −10° C. 2-(bromomethyl)furan (0.02 ml, 0.17 mmol), ethylchloroformate (0.02 ml, 15 mmol), and triethylamine (0.02 ml, 0.15 mmol) were loaded thereto. After stirring the reaction mixture at room temperature for 30 minutes, water was poured in to terminate the reaction. The reactant was extracted with ethylacetate (EA), and the extracted organic layer was dried over magnesium sulfate, followed by concentration under reduced pressure. The concentrated reactant was purified by column chromatography (silica, dichloromethane/methanol) to give the target compound (49 mg, 70%).

$^1$H NMR (400 MHz, $CDCl_3$): δ 8.37 (1H, s), 8.07 (1H, s), 8.00-8.02 (1H, m), 7.83 (1H, d), 7.45 (1H, t, J=8.4 Hz), 6.96 (2H, d), 6.34 (3H, d), 6.31-6.33 (1H, m), 6.21 (1H, d), 5.89 (1H, s), 4.61 (2H, s), 4.44 (2H, d), 3.93 (3H, s), 1.98 (2H, s), 1.89-1.90 (8H, m), 1.74 (2H, s).

Example 2

Preparation of methyl-3-(2-(4-(4-((3,4-dimethoxy-benzyloxy)carbonyl)adamantane-1-yl)phenoxy)acetamido)benzoate

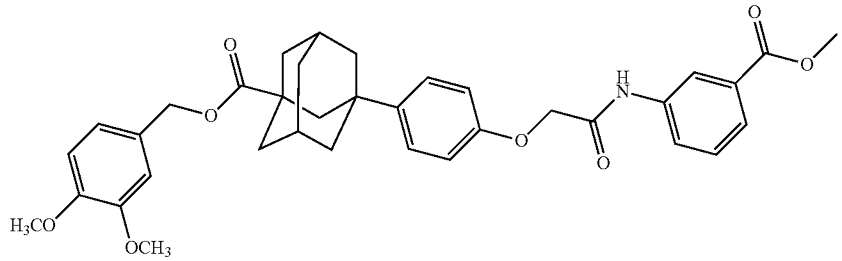 [SMILES: COC(=O)c1cccc(NC(=O)COc2ccc(C34CC5CC(CC(C(=O)OCc6ccc(OC)c(OC)c6)(C5)C3)C4)cc2)c1]

The compound (307.9 mg, 0.66 mmol) prepared in Manufacturing Example 8, 3,4-dimethoxybenzylalcohol (0.14 ml, 0.99 mmol), 1-(3-dimethylaminopropyl)-3-ethylcarbodiimide hydrochloride (189.8 mg, 0.99 mmol), 1-hydroxybenzotriazole hydrate (133.8 mg, 0.99 mmol), and N,N-diisopropylethylamine (0.17 ml, 0.99 mmol) were dissolved in dimethylformamide at room temperature, followed by stirring for overnight. Upon completion of stirring, water was added thereto to terminate the reaction, followed by extraction with ethylacetate (EA). The extracted organic layer was dried over anhydrous magnesium sulfate, followed by concentration under reduced pressure. The concentrated reactant was purified by column chromatography (silica gel, dichloromethane/ethylacetate) to give the target compound (368.6 mg, 91%).

$^1$H NMR (400 MHz, $CDCl_3$): δ 8.38 (1H, s), 8.08 (1H, s), 8.01 (1H, d), 7.83 (1H, d), 7.45 (1H, t, J=8.0 Hz), 6.90-6.94 (3H, m), 6.85 (2H, d), 5.06 (1H, s), 4.61 (1H, s), 3.93 (3H, s), 3.88 (1H, s), 2.20 (1H, s), 1.98 (1H, s), 1.94 (1H, s), 1.88 (81, s), 1.73 (1H, s).

Experimental Example 1

Inhibition of Transcriptional Activation Mediated by HIF-1

The following experiment was performed to investigate the antagonism of the disubstituted adamantyl derivative of the invention with accumulation of HIF-1α.

The compound that can inhibit HRE transcriptional activity mediated by HIF-1α under hypoxia is also able to inhibit metastasis and cancer cell proliferation. Thus, the present inventors first investigated the inhibition of HRE transcriptional activity to confirm HIF-1α suppression. Particularly, to determine the suppression of HRE transcriptional activity by the compounds prepared in Example 1 and Example 2, HRE (Hypoxia Responsive Element, 5'-ACGTG-3') located in human VEGFA gene was duplicated 6 copies in the multi-cloning site of pGL3-basic vector (Promega) using luciferase as a reporter, resulting in the construction of pGL3-HRE-luciferase.

The human colorectal carcinoma cell line HCT116 (ATCC #: CCL-247) was seeded in a 48-well cell culture plate. On the next day, the cells were transfected with ng of pGL3-HRE-luciferase vector and 2.5 ng of Renilla, the control vector, by using polyfect reagent. After 24 hours of culture, the medium was replaced, followed by further culture for 4 hours. The cells were treated with the compounds prepared in Example 1 and Example 2 of the invention at the concentrations of 0, 0.3125, 0.623, 1.25, 2.5, 5, and 10 μM, followed by culture for 12 hours under hypoxia ($O_2$ 1%, $N_2$ 94%, $CO_2$ 5%). Cell lysate was obtained by using RIPA buffer, followed by the measurement of the luciferase activity induced under hypoxia by dual-luciferase assay (Promega), measuring HRE inhibition activity of the compound of Example 2. The results are shown in FIG. 1.

As shown in FIG. 1, the compounds prepared in Examples of the present invention were able to inhibit HRE transcription in dose-dependent manner. In particular, $IC_{50}$ of the compound prepared in Example 2 was 0.86 μM, indicating significant HRE transcription inhibition effect. Therefore, the compounds of the present invention were confirmed to be excellent in inhibition of HRE transcription by HIF-1α induced under hypoxia.

The adamantyl derivative of the present invention is excellent in suppression of HIF-1α related to metastasis and proliferation of cancer cells, suggesting it can be efficiently used as a pharmaceutical anticancer composition or a pharmaceutical composition inhibiting metastasis.

Experimental Example 2

Inhibition of HIF-1α Accumulation Under Hypoxia

The following experiment was performed to investigate the inhibition of HIF-1α accumulation induced by the disubstituted adamantyl derivative of the invention under hypoxia.

In this experiment, it was investigated whether or not the accumulation of HIF-1α could be inhibited by the compound prepared in Example 2 demonstrating excellent inhibition effect of HRE transcription in the HCT116 and HT1080. First, HCT116 (ATCC #: CCL-247) and HT1080 (ATCC #CCL-121) were seeded in cell culture vessels at the density of $2\times10^5$ cell/ml, followed by culture for 24 hours. The cells were then pre-treated under hypoxia ($O_2$ 1%, $N_2$ 94%, $CO_2$ 5%) for 4 hours to induce the accumulation of HIF-1α. Then, the cells were treated with the compound prepared in Example 2 at the concentrations of 0, 1, 3, and 10 μM, followed by culture for 12 hours under hypoxia. Cell extract was prepared by using RIPA buffer. At this time, to compare the expression of HIF-1 target gene under hypoxia, the control having oxygen 20% was prepared. The nuclear extract 30 μg was separated from each sample by SDS-PAGE (sodium dodecyl sulfate-polyacrylamide gel electrophoresis), which was transferred onto polyvinylidene fluoride membrane. Then, HIF-1α protein therein was measured by using HIF-1α antibody (R&D System) and HRP (horseradish peroxidase) labeled secondary antibody (Amersham-Pharmacia). GAPDH (glyceraldehyde 3-phosphate dehydrogenase) was used as the control protein. The results are shown in FIG. 2.

Figure 2:
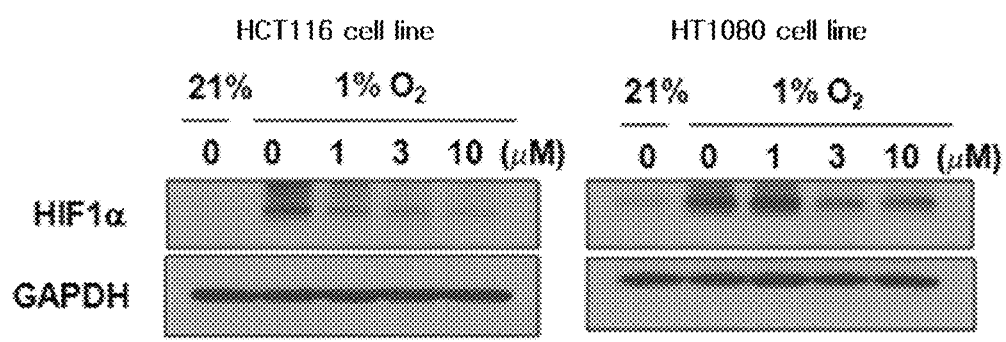
FIG. 2 is a photograph illustrating the inhibitory effect of the compound prepared in Example 2 according to the concentration thereof on the accumulation of HIF-1α under hypoxia.

As shown in FIG. 2, the compound prepared in Example 2 did not affect the generation of GAPDH, while the compound did inhibit the accumulation of HIF-1α induced under hypoxia in a dose-dependent manner. From the above results, it was confirmed that the compound of the present invention can inhibit the expression of HIF-1α by suppressing the accumulation of HIF-1α induced under hypoxia in cancer cells.

Since the disubstituted adamantyl derivative of the present invention is significant in inhibiting the accumulation of HIF-1α that is involved in metastasis and proliferation of cancer cells, the compound can be efficiently used as a pharmaceutical anticancer or antimetastasis composition.

Experimental Example 3

Inhibitory Effect of the Compound of the Invention on the Expression of Metastasis Related Gene The following experiment was performed to investigate whether or not the disubstituted adamantyl derivative of the present invention inhibited the expression of metastasis related gene by suppressing the expression of HIF-1α.

First, the human colorectal carcinoma cell line HCT116 (ATCC #: CCL-247) was seeded in cell culture vessels at the density of $2\times10^5$ cell/ml, followed by culture for 24 hours. The cells were then pre-treated under hypoxia ($O_2$ 1%, $N_2$ 94%, $CO_2$ 5%) for 4 hours to induce the accumulation of HIF-1α. Then, the cells were treated with the compound of the invention at the concentrations of 0, 1, 3, and 10 μM, followed by culture for 12 hours under hypoxia. RNA was purified using trizol. To compare the expression of HIF-1 target gene under hypoxia, the control containing oxygen 20% was prepared. The amount of mRNAs of EMT related genes such as MMP2 and MMP9 and uPA, metastasis related genes induced by HIF-1α, were measured by RT-PCR kit (Invitrogen). At this time, GAPDH, as an internal gene, was simultaneously amplified to investigate the selective inhibition activity of the compound prepared in Example 2 against MMP2, MMP9, and uPA. The results are shown in FIG. 3.

Figure 3:
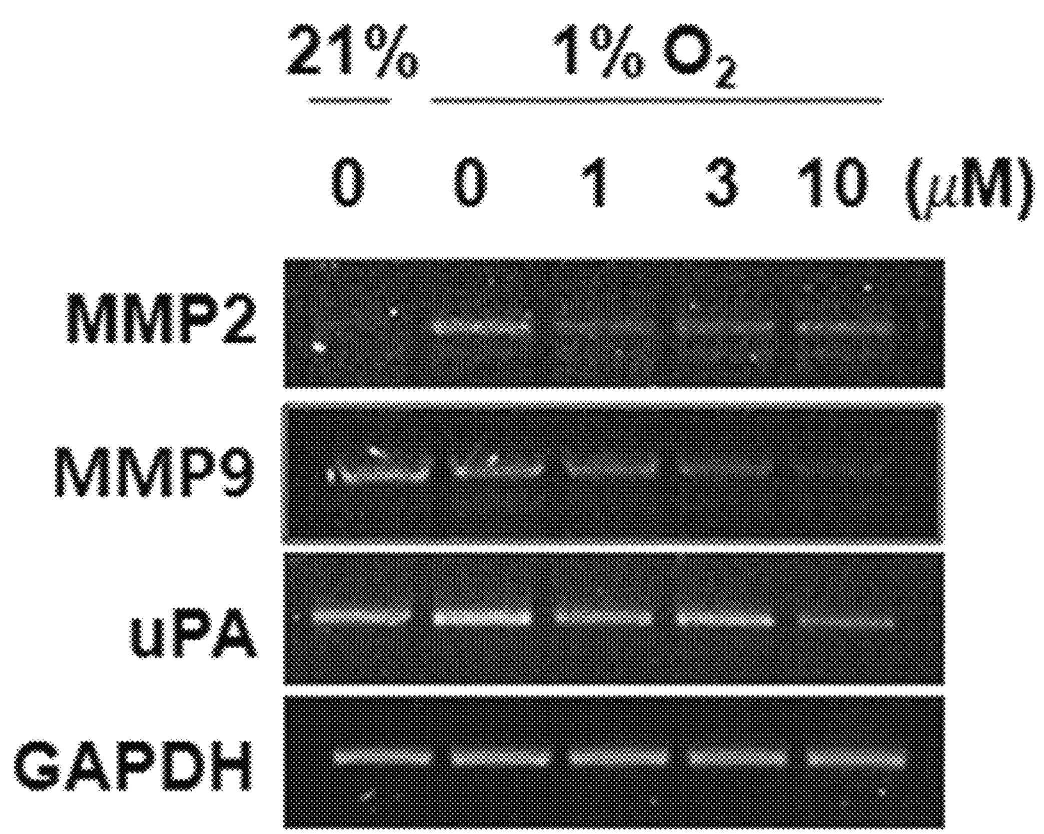
FIG. 3 is a photograph illustrating the inhibitory effect of the compound prepared in Example 2 on the transcription of the metastasis related genes such as MMP2, MMP9, and uPA by suppressing HIF-1 according to the concentration.

As shown in FIG. 3, the compound prepared in Example 2 inhibited expression of MMP2, MMP9, and uPA by inhibiting accumulation of HIF-1α under hypoxia. In particular, the expressions of MMP2 and MMP9 were significantly inhibited by the compound prepared in Example 2 in a dose-dependent manner.

Therefore, the disubstituted adamantyl derivative of the present invention can be efficiently used as a pharmaceutical composition of drugs for anticancer or antimetastasis, since it can inhibit expression of EMT proteins stimulating metastasis by suppressing HIF-1α.

Experimental Example 4

Inhibitory Effect of the Compound of the Invention on the Induction of EMT

The inhibitory effect of the present invention was evaluated on the induction of EMT using EMT inducing proteins such as β-catenin, RohA, vimentin, and Twist.

First, the human colorectal carcinoma cell line HCT116 (ATCC #: CCL-247) was seeded in cell culture vessels at the density of $2\times10^5$ cell/ml, followed by culture for 24 hours. The cells were then pre-treated under hypoxia ($O_2$ 1%, $N_2$ 94%, $CO_2$ 5%) for 4 hours to induce the accumulation of HIF-1α. Then, the cells were treated with the compound of the invention at the concentrations of 0, 1, 3, and 5 μM, followed by culture for 12 hours under hypoxia. Cell extract was prepared by using RIPA buffer. At this time, to compare the expression of HIF-1 target gene under hypoxia, the control having oxygen 20% was prepared. The nuclear extract 30 μg was separated from each sample by SDS-PAGE (sodium dodecyl sulfate-polyacrylamide gel electrophoresis), which was transferred onto polyvinylidene fluoride membrane. Then, the amount of β-catenin, RhoA, vimentin, and Twist was measured by using the primary antibody against each of β-catenin, RhoA, vimentin, and Twist, and HRP (horseradish peroxidase) labeled secondary antibody (Amersham-Pharmacia). GAPDH (glyceraldehyde 3-phosphate dehydrogenase) was used as the control protein. The results are shown in FIG. 4.

Figure 4:
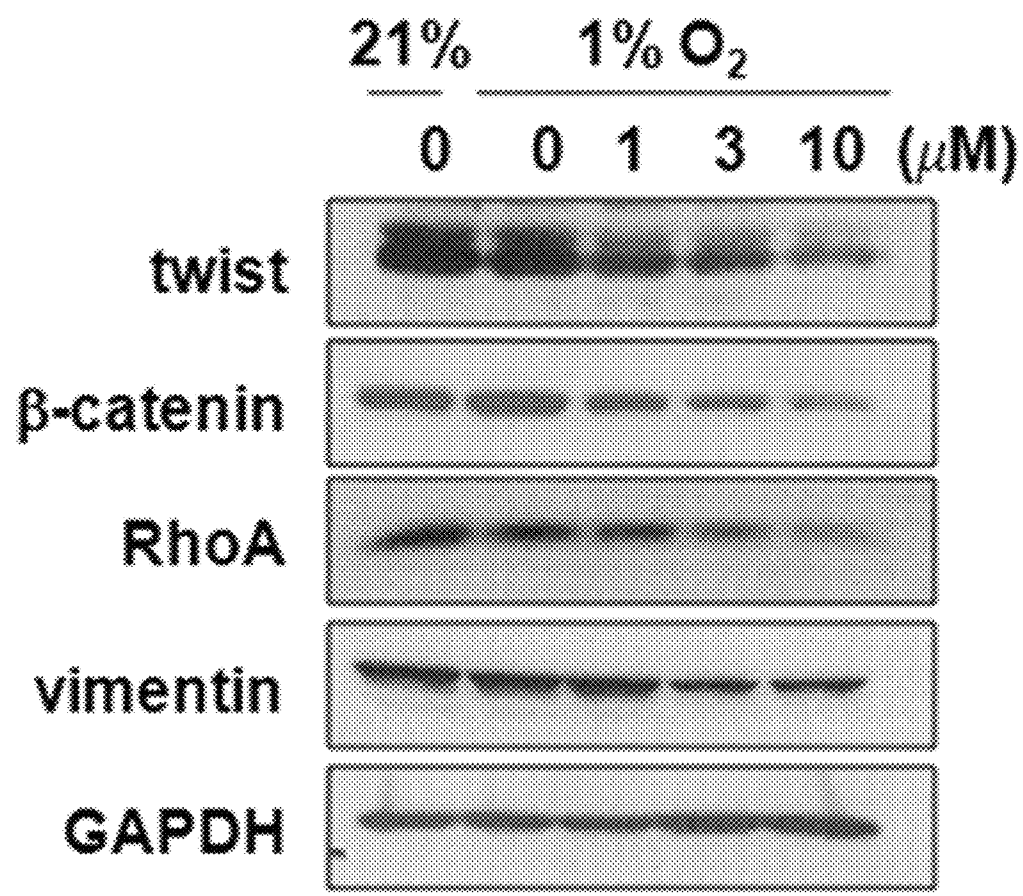
FIG. 4 is a photograph illustrating the inhibitory effect of the compound prepared in Example 2 according to the concentration thereof on the expression of the EMT promoting gene including Twist under hypoxia.

As shown in FIG. 4, the compound prepared in Example 2 inhibited the metastasis related protein Twist. The compound also inhibited the expression of β-catenin and RhoA that regulates cancer cell metastasis. The inhibition of the expression of the metastasis related protein by the compound prepared in Example 2 was not attributed to its non-selective cytotoxicity but attributed to the selective inhibition of the expression of Twist.

Therefore, the disubstituted adamantyl derivative of the present invention can be efficiently used as a pharmaceutical anticancer or antimetastasis composition, since it can inhibit the activity of Twist to inhibit the expression of the metastasis related proteins by suppressing accumulation of HIF-1α.

Experimental Example 5

Inhibitory Effect of the Compound of the Invention on Cell Migration

The following experiment was performed to evaluate the inhibitory effect of the compound prepared in Example 2 on cell migration.

First, an insert (Ibidi) was placed in the center of a 6-well culture plate by using a pincette. 70 μl of the human colorectal carcinoma cell line HCT116 was loaded in each well at the density of $3\times10^5$ cell/ml. Medium was filled around the insert. 24 hours later, the insert was carefully removed by using a pincette. The cells were carefully washed with medium not to be fallen off to the bottom. Then, the diluted medium supplemented with the compound prepared in Example 2 (0.4 μM) was added thereto. 48 hours later, cell migration was observed under microscope. At this time, the medium containing dimethylsulfoxide (DMSO) was used for the non-treated group. Cell migration was photographed by using real-time cell analyzer (Applied Biophysics). First, 100 μl of cysteine solution was loaded in a 8-well plate, which stood at room temperature for 10 minutes. $2\times10^5$ HCT116 cells were suspended in 300 μl of medium. Cysteine solution was eliminated and then the cells were added, followed by culture in a 37° C. incubator for 15 hours. When saturation of the cell was confirmed on the graph of real-time cell analyzer, a round wound was made by electric shock. Then, the medium was replaced with the medium supplemented with the compound prepared in Example 2 (10 μM). The cell growth around the round wound was observed. Time that had taken for the round wound to be filled up with new grown cells was measured and compared with that of the control, which was calculated on the graph. The results are shown in FIG. 5 and FIG. 6.

Figure 5:
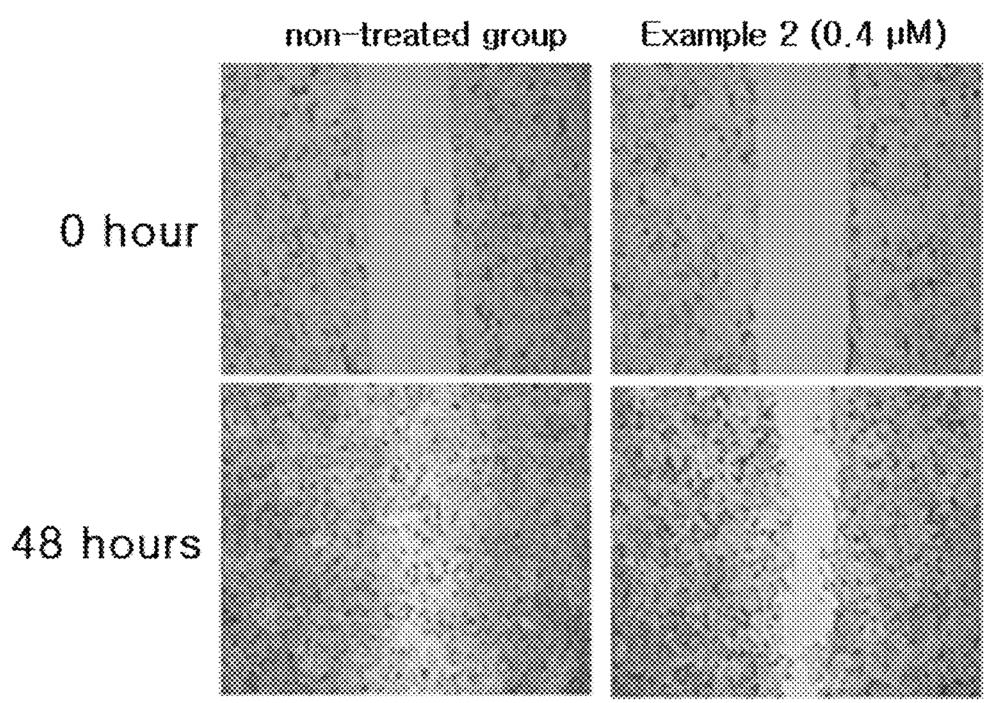
FIG. 5 is a photograph illustrating the inhibition of cancer cell migration in the group treated with the compound of Example 2.
Figure 6:
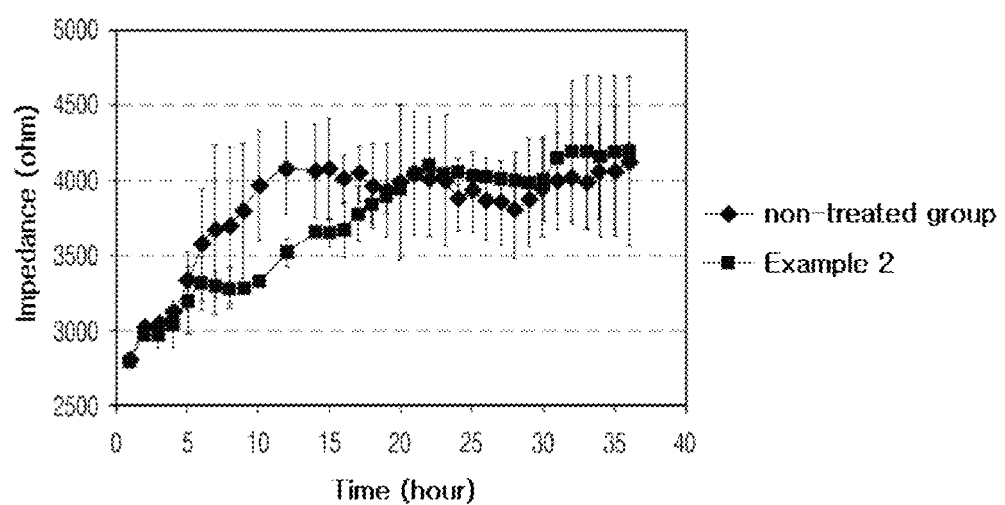
FIG. 6 is a graph illustrating the time-dependent cancer cell migration observed in the group treated with the compound of Example 2.

As shown in FIG. 5 and FIG. 6, in the cancer cells treated with the compound of the invention, cell migration was inhibited so that the round wound remained unfilled. In the meantime, in the non-treated group, cell migration was confirmed and the round wound was filled up. From the graph obtained by real-time cell analyzer, it was confirmed that time for cell migration in the non-treated group was 11.5 hours, which was comparatively short, while the time for cell migration in the cells treated with the compound prepared in Example 2 of the invention was 22 hours, which was almost double the time of the non-treated group, indicating at least double the cell migration inhibiting effect.

The disubstituted adamantyl derivative of the present invention inhibited cancer cell migration by suppressing the expression of HIF-1α. The cancer cell migration inhibiting effect of the disubstituted adamantyl derivative of the invention was almost twice as high as that of the control group not-treated with the compound, so that the compound of the invention can be efficiently used as a pharmaceutical anticancer or antimetastasis composition.

Experimental Example 6

Inhibitory Effect of the Compound of the Invention on Cell Invasion

The following experiment was performed to evaluate the inhibitory effect of the disubstituted adamantyl derivative of the present invention on cell invasion.

A cell culture insert (BD Falcon, 8-m pore size) was fixed on a 24-well plate, to which 100 μl of matrigel diluted in 20 fold was added, which stood at 37° C. for at least 1 hour. 700 μl of medium supplemented with 10% FBS was loaded in each well of the 24-well plate under the insert. HT1080 cells ($1\times10^5$) displaying high metastatic activity were suspended in 300 μl of serum-free medium. The cells were treated with the compound of the invention at the concentrations of 0, 10, and 20 μM. The 300 cells treated with the compound of the invention were placed in the insert, followed by culture in a 37° C. incubator for hours. The insert was taken out and fixed in 10% formalin solution. The cells remaining in the inside of the insert were eliminated by using cotton swab, followed by washing with water. The cells were stained with sulforhodamine B for 1 hour, and then washed with acetic acid, which were then dried. The cells were photographed under optical microscope and cell invasion was observed. Also, a membrane was sliced and dissolved in 10 mM Tris solution, followed by measuring $OD_{540}$. The results are shown in FIG. 7.

Figure 7:
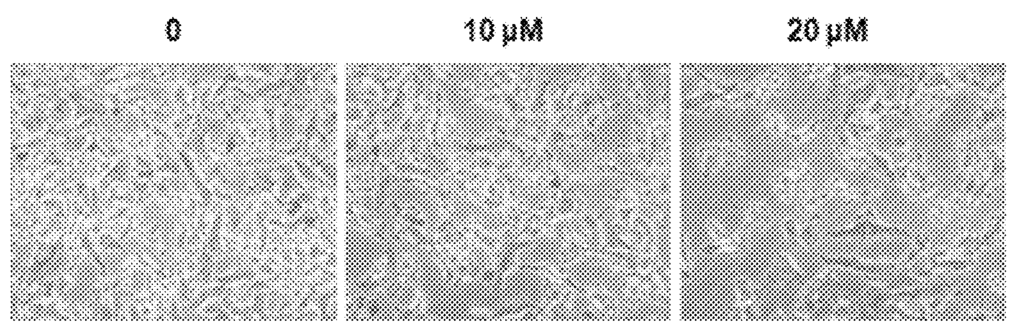
FIG. 7 is a photograph illustrating the inhibition of cancer cell invasion in the group treated with the compound of Example 2.

As shown in FIG. 7, invasion of HT1080 cells treated with the compound prepared in Example 2 was not observed and cell morphology was still maintained. Therefore, it was confirmed that the compound of the present invention inhibited metastasis by suppressing the cell invasion of HT1080 cells having high metastatic activity.

Therefore, the disubstituted adamantyl derivative of the present invention can be efficiently used as a pharmaceutical anticancer or antimetastasis composition, since it is excellent in inhibiting cell invasion and accordingly excellent in inhibiting metastasis.

Experimental Example 7

In Vivo Inhibition of Cancer Cell Proliferation in the Mouse by Intraperitoneal Administration of the Compound of the Invention The following experiment was performed to evaluate the inhibitory effect of the disubstituted adamantyl derivative of the present invention on cancer cell proliferation via intraperitoneal administration.

First, female Balb/c nude mice (6 weeks old) were administered with the compound prepared in Example 2 via intraperitoneal injection. After generating a tumor in the nude mouse by transplanting the human colorectal carcinoma cell line HCT116, the compound prepared in Example 2 was intraperitoneally administered at the concentration of 30 mg/kg for 1 week. One week later, any change in the tumor size was observed by comparing the volume of the first formed tumor and the volume measured one week after. On the last day, the tumor was weighed. To investigate toxicity of the compound, any general symptoms along with the weight changes in the animal were observed during the administration period. At this time, an excipient was treated to the non-treated group, and sunitinib (30 mg/kg) was administered to the positive control. All the values of each measurement title were examined by t-test to investigate the statistical significance of the values obtained from the non-treated group, the group treated with the compound of Example 2, and the positive control group. The results are shown in Table 1, Table 2, and FIG. 8.

TABLE 1

| | Tumor volume over the administration time ($V_t - V_o$) (Inhibition rate of tumor growth (%)) | | | | Tumor weight at final day (mg) (Inhibition rate of tumor growth (%)) |
|---|---|---|---|---|---|
| | 0 day | 2 days | 4 days | 4 days | 7 days |
| Non-treated group | 0.0 ± 0.0 | 22.8 ± 2.5 | 72.2 ± 7.3 | 334.9 ± 44.6 | 1689.6 ± 227.3 |
| Compound of Example 2 | 0.0 ± 0.0 (0%) | 18.5 ± 2.5* (18.9%) | 57.5 ± 6.7** (20.3%) | 262.6 ± 38.5* (21.6%) | 1318.7 ± 220.9* (22.0%) |
| Positive control (sunitinib) | 0.0 ± 0.0 (0%) | 15.6 ± 4.3* (31.7%) | 47.5 ± 10.7** (34.2%) | 205.4 ± 35.2*** (38.7%) | 1064.9 ± 130.9*** (37.0%) |

1 significant (t-Test):
*p < 0.05,
**p < 0.01,
***p < 0.001 (compare to non-treated group)

TABLE 2

| | Weight changes over the administration time (%) | | | |
|---|---|---|---|---|
| | 0 day | 2 days | 4 days | 7 days |
| Non-treated group | 100.0 ± 0.0 | 101.7 ± 0.8 | 102.2 ± 01.8 | 102.3 ± 3.0 |
| Compound of Example 2 | 100.0 ± 0.0 | 100.4 ± 1.3 | 100.8 ± 1.2 | 99.9 ± 1.3 |
| Positive control (sunitinib) | 100.0 ± 0.0 | 100.5 ± 1.4 | 100.7 ± 2.0 | 100.8 ± 3.3 |

Figure 8:
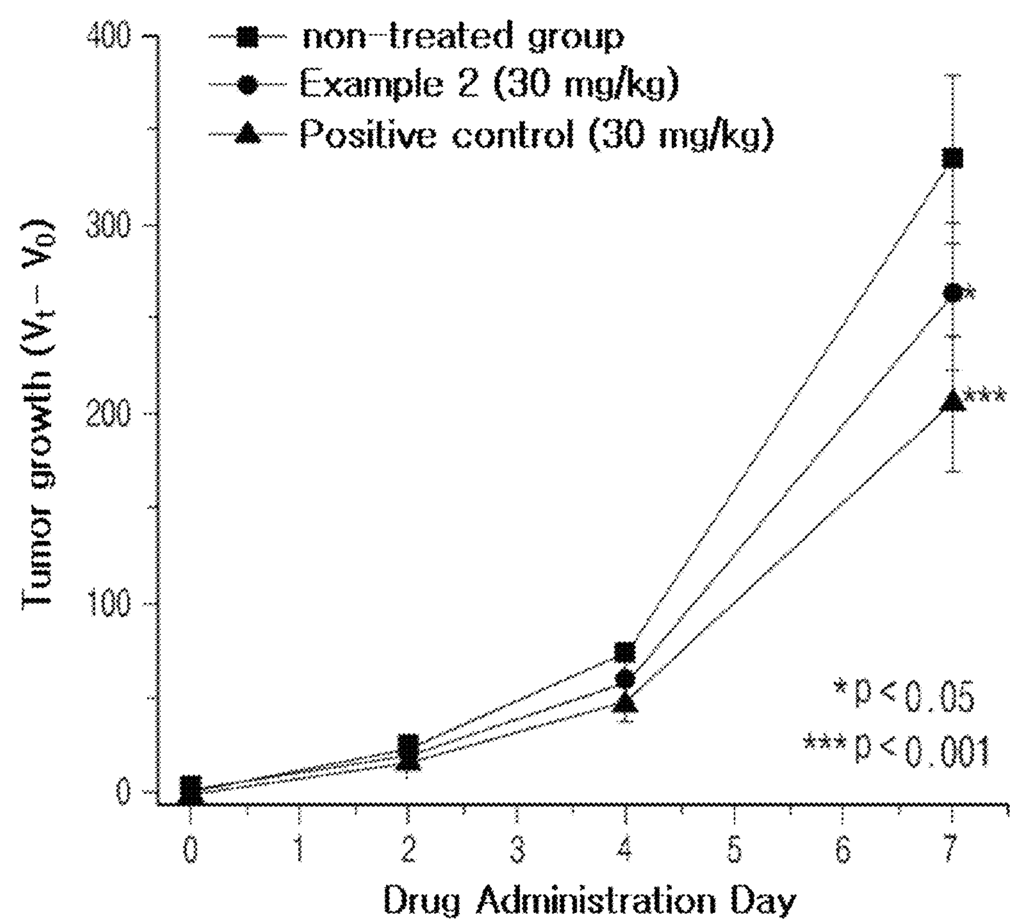
FIG. 8 is a graph illustrating the tumor volume changes over the time after the administration of the compound of Example 2.

As shown in Table 1, Table 2, and FIG. 8, when the compound prepared in Example 2 of the invention was administered alone, the inhibitory effect on tumor growth was 22%. When sunitinib was administered in the positive control, the inhibitory effect on tumor growth was 37%. During the administration of the compound of Example 2, none of specific symptoms were observed in the nude mice. The weights of the mice were not much changed or not much different from that of the non-treated group even after 7 days from the administration. Therefore, it was confirmed that the compound of the present invention had the inhibiting activity of cancer cell proliferation without cytotoxicity.

The disubstituted adamantyl derivative of the present invention was excellent in inhibiting cancer cell proliferation without cytotoxicity, indicating that it is safe in human to be used as a pharmaceutical anticancer or antimetastasis composition.

Experimental Example 8

Evaluation of Inhibition of Metastasis In Vivo in the Test Mouse

The following experiment was performed to investigate the inhibition of metastasis by the disubstituted adamantyl derivative of the present invention in the test animal administered with the compound via intraperitoneal injection.

To evaluate the inhibition effect of the compound on metastasis, C57BL/6 mice were transplanted with B16F10 melanoma cells ($2\times10^6$ cells/ml) expressing luciferase via intravenous injection (0.2 ml, $4\times10^5$ cells/mouse). One hour later, 50 μl of luciferin was administered to each mouse at the concentration of 15 mg/ml via intraperitoneal injection. Then, the compound prepared in Example 2 of the invention was intraperitoneally administered at the concentration of 50 mg/kg 13 times. At this time, dimethylsulfoxide (DMSO) was treated to the non-treated group, and sunitinib (30 mg/kg), the conventional anticancer agent, was administered to the positive control. The image of the mouse was photographed every day for 14 days with a live animal imaging system (PHOTON IMAGER, Biospace). On the last day of the experiment, the mouse was sacrificed by using $CO_2$ gas. The lung was extracted from the mouse, and lung metastasis of the skin cancer cells was confirmed. To investigate toxicity, weight and other general symptoms were observed during the experimental period. At this time, all the values of each measurement title were examined by t-test for the statistical significance of the values obtained from the non-treated group, the group treated with the compound of Example 2, and the positive control group. The results are shown in Table 3, Table 4, FIG. 9, and FIG. 10.

TABLE 3

| | Image signals over the administration time (photons/s/sr) (Inhibition rate of tumor metastasis (%)) | | | | Image signal at final day (Inhibition rate of tumor metastasis (%)) |
|---|---|---|---|---|---|
| | 0 day | 4 days | 9 days | 14 days | 14 days |
| Non-treated group | 557.2 ± 407.2 | 164.3 ± 66.1 | 666.5 ± 1080.4 | 32145.5 ± 31121.3 | 81962.6 ± 53648.4 |
| Compound of Example 2 | 1112.8 ± 1015.6 | 157.8 ± 23.2 (3.9%) | 392.3 ± 534.8 (41.1%) | 4740.0 ± 1920.5* (85.3%) | 14751.2 ± 9987.8** (82.0%) |
| Positive control (sunitinib) | 857.2 ± 679.3 | 222.0 ± 146.1 | 47.5 ± 10.7 (19.9%) | 13084.0 ± 8931.2 (59.3%) | 21738.7 ± 14939.0 (73.4%) |

significant (t-Test):
*p < 0.05,
**p < 0.01 (compare to non-treated group)

TABLE 4

| | Weight changes over the administration time (%) | | | | | | |
|---|---|---|---|---|---|---|---|
| | 0 day | 2 days | 4 days | 7 days | 9 days | 11 days | 14 days |
| Non-treated group | 100.0 ± 0.0 | 101.1 ± 4.7 | 102.7 ± 3.0 | 104.5 ± 4.7 | 104.2 ± 6.0 | 107.3 ± 6.2 | 108.0 ± 3.9 |
| Compound of Example 2 | 100.0 ± 0.0 | 102.7 ± 3.8 | 103.6 ± 2.8 | 103.9 ± 2.6 | 106.4 ± 3.6 | 111.1 ± 4.7 | 111.2 ± 7.6 |
| Positive control (sunitinib) | 100.0 ± 0.0 | 100.9 ± 2.2 | 102.9 ± 2.0 | 103.0 ± 2.8 | 106.0 ± 3.1 | 105.4 ± 2.9 | 107.7 ± 3.3 |

Figure 9:
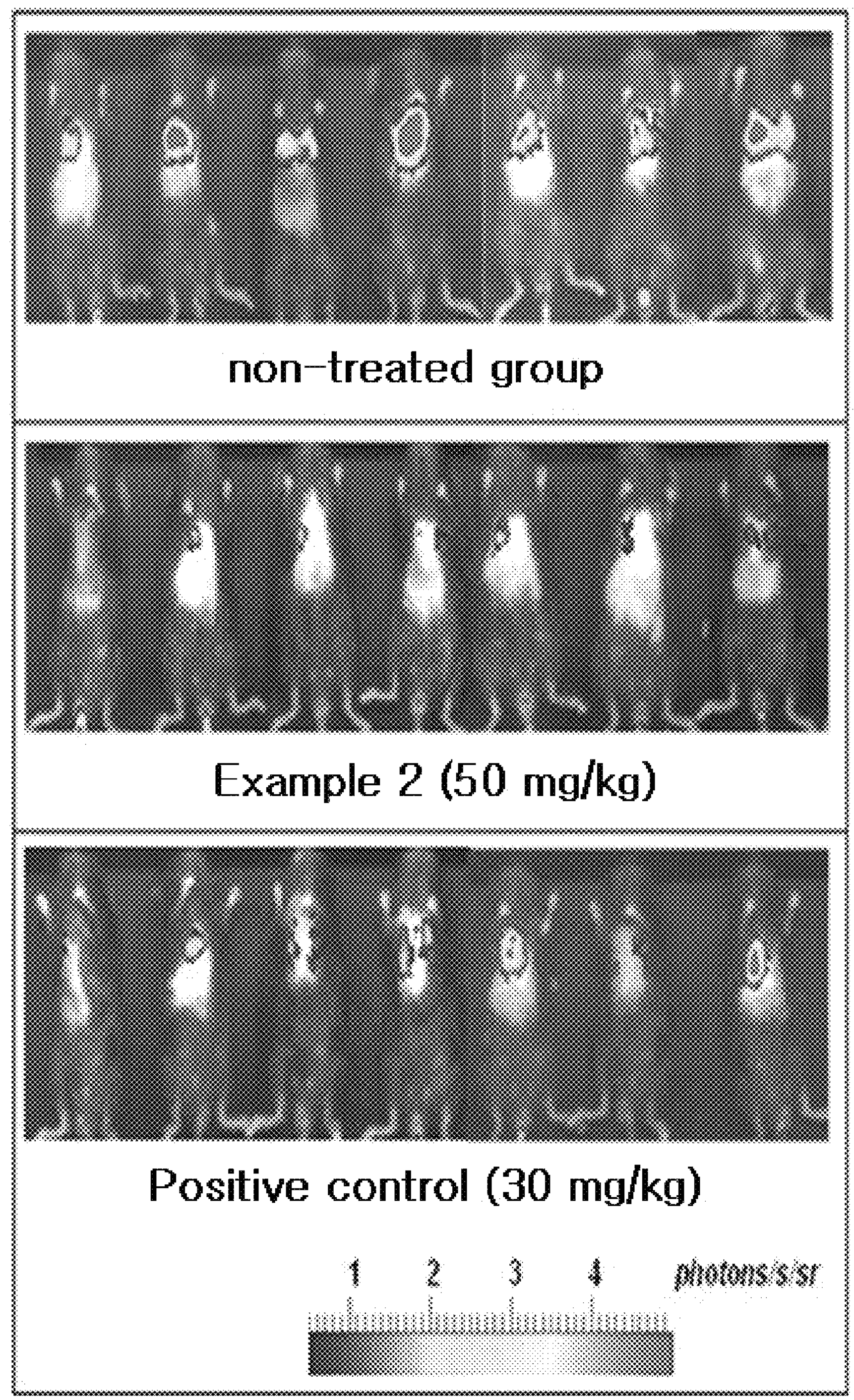
FIG. 9 is a photograph illustrating the inhibition of metastasis over the administration time in the non-treated group, in the group treated with the compound of Example 2, and in the positive control group, observed by image signal measurement.
Figure 10:
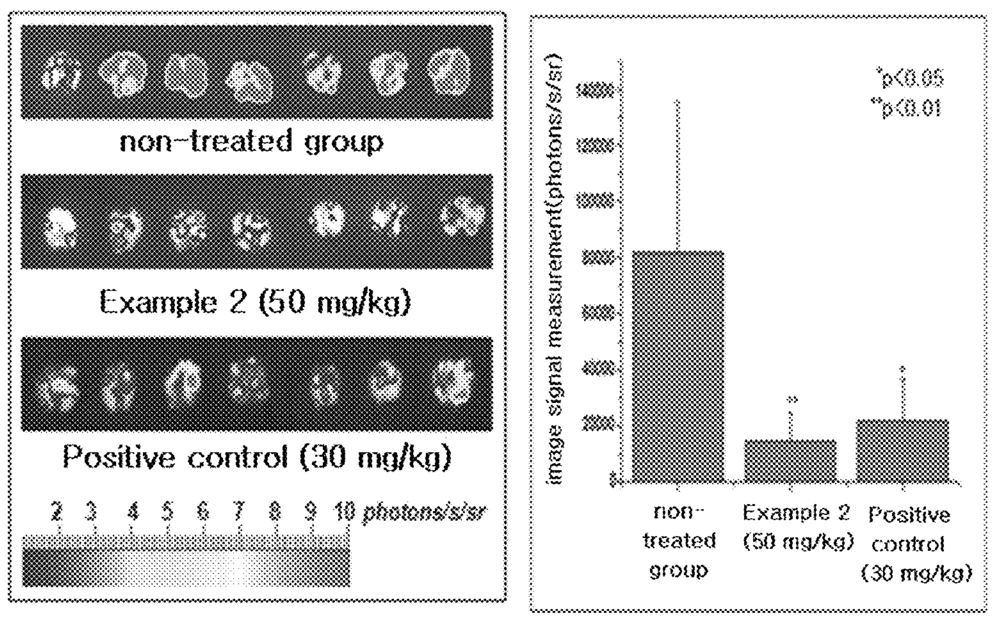
FIG. 10 is a photograph illustrating the inhibition of metastasis in the lung tissue extracted from the nude mouse according to Experimental Example 8, observed by image signal measurement.

As shown in Table 3, Table 4, FIG. 9, and FIG. 10, the experimental group treated with the compound prepared in Example 2 displayed the metastasis inhibiting effect by 85.3% (p<0.05), compared with that of the non-treated treated group according to the signal (photons/s/sr). In the meantime, the positive control displayed the inhibition of metastasis by 59.3%. On the last day, the lung was extracted from the mouse, followed by imaging. In the experimental group treated with the compound of Example 2, metastasis was inhibited by 82.0% (P<0.01). In the positive control group, metastasis was inhibited by 73.4% (P<0.05). Specific symptoms were not observed in the mouse treated with the compound of Example 2 during the whole period of experiment. The mouse body weight was not much changed or reduced, either, compared with that of the non-treated group until the last day (day 14). Therefore, it can be concluded that the inhibition of metastasis by the compound of the present invention is more significant than the conventional anticancer agent, sunitinib. Further, the compound of the invention is confirmed to be safe without cytotoxicity.

The disubstituted adamantyl derivative of the present invention inhibited accumulation of HIF-1α, thereby inhibited the expression of the metastasis related protein Twist, leading inhibition of the metastasis related proteins, β-catenin, and RohA, and EMT related genes such as MMP2 and MMP9, suggesting excellent inhibition effect of the invented compound on cancer cell metastasis. In addition, the compound of the invention displays no cytotoxicity mediated side effects when it is absorbed in a living body. Therefore, it can be efficiently used as a pharmaceutical anticancer or antimetastasis composition.

The disubstituted adamantyl derivative represented by formula 1 of the present invention can be formulated in various forms according to the purpose of use. The followings are some examples of different formulations of the composition comprising the compound represented by formula 1 as an active ingredient, but the present invention is not limited thereto.

Manufacturing Example 1

Preparation of Powders

| | |
|---|---|
| Compound of formula 1 | 2 g |
| Lactose | 1 g |

Powders were prepared by mixing all the above components, which were filled in airtight packs according to the conventional method for preparing powders.

Manufacturing Example 2

Preparation of Tablets

| | |
|---|---|
| Compound of formula 1 | 100 mg |
| Corn starch | 100 mg |
| Lactose | 100 mg |
| Magnesium stearate | 2 mg |

Tablets were prepared by mixing all the above components by the conventional method for preparing tablets.

Manufacturing Example 2

Preparation of Capsules

| | |
|---|---|
| Compound of formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4

Preparation of Injections

| | |
|---|---|
| Compound of formula 1 | 100 mg |
| Mannitol | 180 mg |
| $Na_2HPO_4 \cdot 2H_2O$ | 26 mg |
| Distilled water | 2974 mg |

Injections were prepared by mixing all the above components by the conventional method for preparing injections.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A disubstituted adamantyl derivative represented by formula 1 or a pharmaceutically acceptable salt thereof:

[Formula 1]

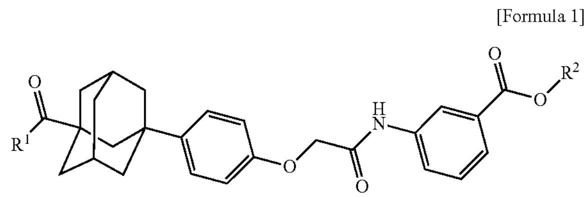

wherein $R^1$ is —X—$(CH_2)_n$—$R^3$;

$R^2$ is H; and $R^3$ is unsubstituted or substituted C5-C10 aryl or unsubstituted or substituted heteroaryl, wherein the heteroaryl is 5-membered or 6-membered heteroaryl having one or more heteroatoms selected from the group consisting of N, O, and S, the substituted aryl or heteroaryl can be substituted with one or more halogens; C1-C6 straight or branched alkyl; hydroxy; C1-C6 straight or branched alkoxy; nitro; nitrile; unsubstituted amine or amine substituted with one or more C1-C6 straight or branched alkyls; C1-C6 straight or branched alkylcarbonyl or 5-membered or 6-membered heterocycloalkyl having heteroatoms selected from the group consisting of N, O, and S;

X is NH or O, provided that when $R^3$ is unsubstituted or substituted aryl X is O; and n is an integer of 1-5.

2. The disubstituted adamantyl derivative represented by formula 1 or a pharmaceutically acceptable salt thereof according to claim 1, wherein:

$R^1$ is —X—$(CH_2)_n$—$R^3$;

$R^2$ is H;

$R^3$ is unsubstituted or substituted phenyl, unsubstituted or substituted pyridine, pyrazine, imidazole, thiophene, benzothiophene, furan, or benzofuran, wherein the substituted phenyl or the substituted pyridine, pyrazine, imidazole, thiophene, benzothiophene, furan or benzofuran is optionally substituted with one or more fluoro, bromo, chloro, methyl, ethyl, propyl, isopropyl, butyl, hydroxy, t-butyl, methoxy, ethoxy, propoxy, butoxy, nitro, nitrile, amine, methylamine, dimethylamine, ethylamine, diethylamine, acetyl, ethylcarbonyl or 5-membered or 6-membered heterocycloalkyl having heteroatoms selected from the group consisting of N, O, and S;

X is NH or O, provided that when $R^3$ is unsubstituted or substituted aryl X is O; and n is an integer of 1-3.

3. A method for preparing a disubstituted adamantyl derivative represented by formula 1 according to claim 1 comprising reacting a compound represented by formula 2 with a compound represented by formula 3 in the presence of a base and a coupling agent to give a compound represented by formula 1, as shown in the below reaction formula 1:

[Reaction Formula 1]

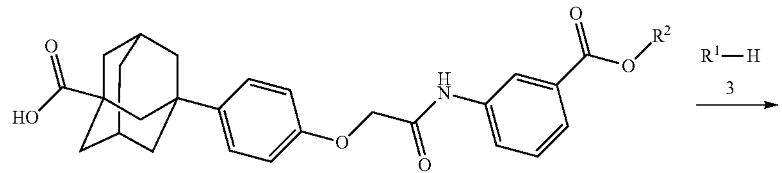

-continued

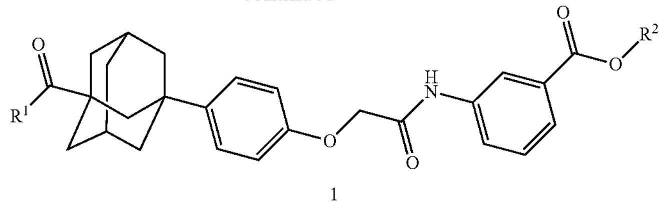

wherein $R^1$ and $R^2$ are the same as defined in claim 1.

4. A pharmaceutical composition comprising an effective amount of a disubstituted adamantyl derivative represented by formula 1 according to claim 1 or a pharmaceutically acceptable salt thereof, in combination with a pharmaceutically acceptable carrier.

5. A method for inhibiting metastasis of a cancer comprising administering to the subject in need thereof an effective amount of a disubstituted adamantyl derivative represented by Formula 1 or a pharmaceutically acceptable salt thereof, wherein the cancer is a solid cancer selected from the group consisting of breast cancer, liver cancer, lung cancer, stomach cancer, kidney cancer, prostate cancer and colorectal cancer:

[Formula 1]

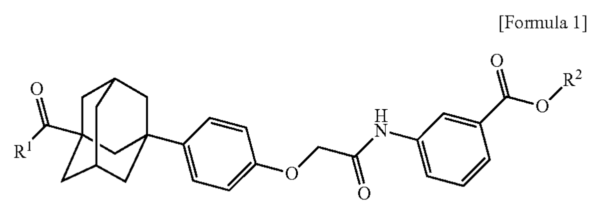

wherein $R^1$ is —X—$CH_2)_n$—$R^3$;

$R^2$ is H or a C1-C6 straight or branched alkyl; and $R^3$ is unsubstituted or substituted C5-C10 aryl or unsubstituted or substituted heteroaryl, wherein the heteroaryl is 5-membered or 6-membered heteroaryl having one or more heteroatoms selected from the group consisting of N, O, and S, the substituted aryl or heteroaryl can be substituted with one or more halogens; C1-C6 straight or branched alkyl; hydroxy; C1-C6 straight or branched alkoxy; nitro; nitrile; unsubstituted amine or amine substituted with one or more C1-C6 straight or branched alkyls; C1-C6 straight or branched alkylcarbonyl or 5-membered or 6-membered heterocycloalkyl having heteroatoms selected from the group consisting of N, O, and S;

X is NH or O, provided that X is O when $R^3$ is unsubstituted or substituted aryl; and n is an integer of 1-5.

6. The method of claim 5, wherein the disubstituted adamantyl derivative or the pharmaceutically acceptable salt thereof inhibits the expression of Twist gene via suppressing accumulation of HIF-1α.

7. A method for inhibiting expression of HIF-1α in a cancer cell of a subject in need thereof, comprising administering to the subject an effective amount of a disubstituted adamantyl derivative represented by Formula 1 or a pharmaceutically acceptable salt thereof, wherein the cancer is a solid cancer selected from the group consisting of breast cancer, liver cancer, lung cancer, stomach cancer, kidney cancer, prostate cancer and colorectal cancer:

[Formula 1]

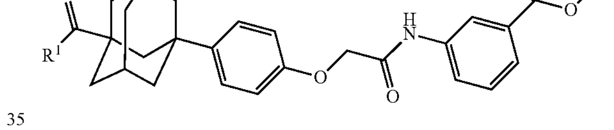

wherein $R^1$ is —X—$(CH_2)_n$—$R^3$;

$R^2$ is H or a C1-C6 straight or branched alkyl; and $R^3$ is unsubstituted or substituted C5-C10 aryl or unsubstituted or substituted heteroaryl, wherein the heteroaryl is 5-membered or 6-membered heteroaryl having one or more heteroatoms selected from the group consisting of N, O, and S, the substituted aryl or heteroaryl can be substituted with one or more halogens; C1-C6 straight or branched alkyl; hydroxy; C1-C6 straight or branched alkoxy; nitro; nitrile; unsubstituted amine or amine substituted with one or more C1-C6 straight or branched alkyls; C1-C6 straight or branched alkylcarbonyl or 5-membered or 6-membered heterocycloalkyl having heteroatoms selected from the group consisting of N, O, and S;

X is NH or O, provided that X is O when $R^3$ is unsubstituted or substituted aryl; and n is an integer of 1-5.

* * * * *